United States Patent [19]
Allen et al.

[11] Patent Number: 5,914,329
[45] Date of Patent: Jun. 22, 1999

[54] DIMESYLATE SALTS OF NEUROPEPTIDE Y LIGANDS

[75] Inventors: Douglas J. M. Allen, New London; Lyle R. Brostrom, Trumbull; Alireza S. Kord; Laurie A. Whipple, both of Groton, all of Conn.

[73] Assignee: Pfizer Inc., New York, N.Y.

[21] Appl. No.: 08/972,470

[22] Filed: Nov. 18, 1997

Related U.S. Application Data

[60] Provisional application No. 60/031,815, Nov. 26, 1996.

[51] Int. Cl.⁶ .......................... A01N 43/60; C07D 241/04
[52] U.S. Cl. ............................................. 514/255; 544/392
[58] Field of Search ............................ 514/255; 544/392

[56] References Cited

FOREIGN PATENT DOCUMENTS

96/14307  5/1996  WIPO .

OTHER PUBLICATIONS

J. Med. Chem., vol. 8, No. 230, 1965, pp. 230–235, V. Harold Maddox, et al.: "The Synthesis of Phencyclidine and Other I–Arylcyclohexylamines".

*Primary Examiner*—Mukund J. Shah
*Assistant Examiner*—Tamthom T. Ngo
*Attorney, Agent, or Firm*—Peter C. Richardson; Gregg C. Benson; Mervin E. Brokke

[57] ABSTRACT

The dimesylate salt of cis-1-(3-ethoxyphenyl)-1-(4-phenylpiperazin-1-yl)4-methyl-cyclohexane has superior properties and is useful to treat physiological disorders associated with an excess of neuropeptide Y.

7 Claims, No Drawings

DIMESYLATE SALTS OF NEUROPEPTIDE Y LIGANDS

This application claims the benefits of U.S. Provisional application No. 60/031,815, filed Nov. 26, 1996.

BACKGROUND OF THE INVENTION

1. Field of the Invention

This invention relates to the dimesylate salt of cis-1-(3-ethoxyphenyl)-1-(4-phenylpiperazin-1-yl)-4-methylcyclohexane (compound I) which selectively binds to mammalian Neuropeptide Y receptors. This invention also relates to pharmaceutical compositions comprising compound I. It further relates to the use of compound I and compositions containing compound I in treating physiological disorders associated with an excess of neuropeptide Y, especially eating disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of Neuropeptide $Y_1$ receptors is related to vasoconstriction, Wahlestedt et al., Regul. Peptides, 13: 307–318 (1986), McCauley and Wesffall, J. Pharmacol. Exp. Ther. 261: 863–868 (1992), and Grundemar et al., Br. J. Pharmacol. 105: 45–50 (1992); and to stimulation of consummatory behavior, Flood and Morley, Peptides, 10: 963–966 (1989), Leibowitz and Alexander, Peptides, 12: 1251–1260 (1991), and Stanley et al., Peptides, 13: 581–587 (1992).

Grundemar and Hakanson, TiPS, May 1994 [Vol. 15], 153–159, state that, in animals, Neuropeptide Y is a powerful stimuli of food intake, and an inducer of vasoconstriction leading to hypertension. They further point out that low levels of Neuropeptide Y is associated with loss of appetite. These reports clearly indicate that compounds that inhibit the activity of this protein will reduce hypertension and appetite in animals.

The dihydrochloride salt of cis-1-(3-ethoxyphenyl)-1-(4-phenylpiperazin-1-yl)-4-methyl-cyclohexane is described in International Application PCT/US95/14472 which is published as WO 96/14307. The disclosure of the International Application is hereby incorporated herein by reference.

SUMMARY OF THE INVENTION

Compounds that interact with NPY1 receptors and inhibit the activity of neuropeptide Y at those receptors are useful in treating physiological disorders associated with an excess of neuropeptide Y such as eating disorders, for example, obesity and bulimia, and certain cardiovascular diseases, for example, hypertension.

The compound encompassed by the instant invention is of the formula:

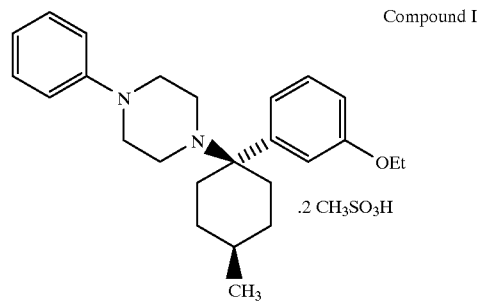

Compound I

In another aspect this invention comprises pharmaceutical compositions comprising compound I and a pharmaceutically acceptable carrier.

In another aspect this invention comprises polymorph A and polymorph B of compound I.

DETAILED DESCRIPTION OF THE INVENTION

Salts of cis-1-(3-ethoxyphenyl)-1-(4-phenylpiperazin-1-yl)-4-methylcyclohexane are readily prepared by the procedures described in WO 96/14307.

The preparation of the required free base is accomplished with a Strecker reaction using 4-methylcyclohexanone, potassium cyanide and 1-phenylpiperazine in water to yield cis and trans 1-cyano-1-(4-phenylpiperazin-1-yl)-4-methylcyclohexane (Maddox, V. Harold, et al., J. Med. Chem. 8: pp. 230 (1965)). Reaction of this material with 3-ethoxyphenylmagnesium chloride in tetrahydrofuran (Bruylants reaction) results in displacement of the cyanide moiety and formation of predominantly trans-1-(3-ethoxyphenyl)-1-(4-phenylpiperazin-1-yl)-4-methylcyclohexane (Maddox, V. Harold, et al., J. Med. Chem. 8: pp. 230 (1965)). The free base was purified by two recrystallizations in ethanol containing a small amount of acetic acid.

The synthetic procedure is illustrated in the following reaction scheme.

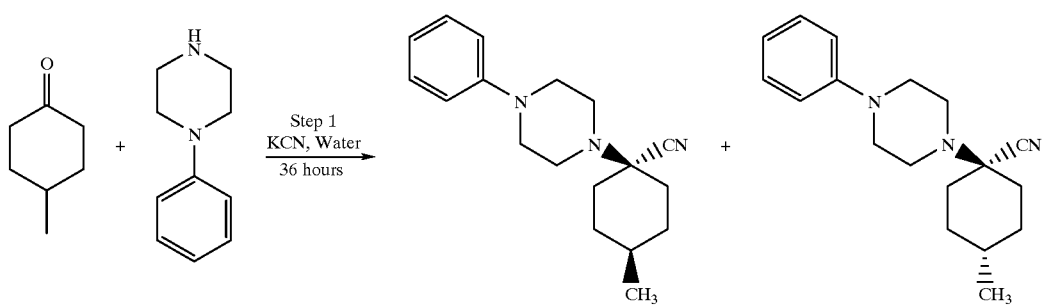

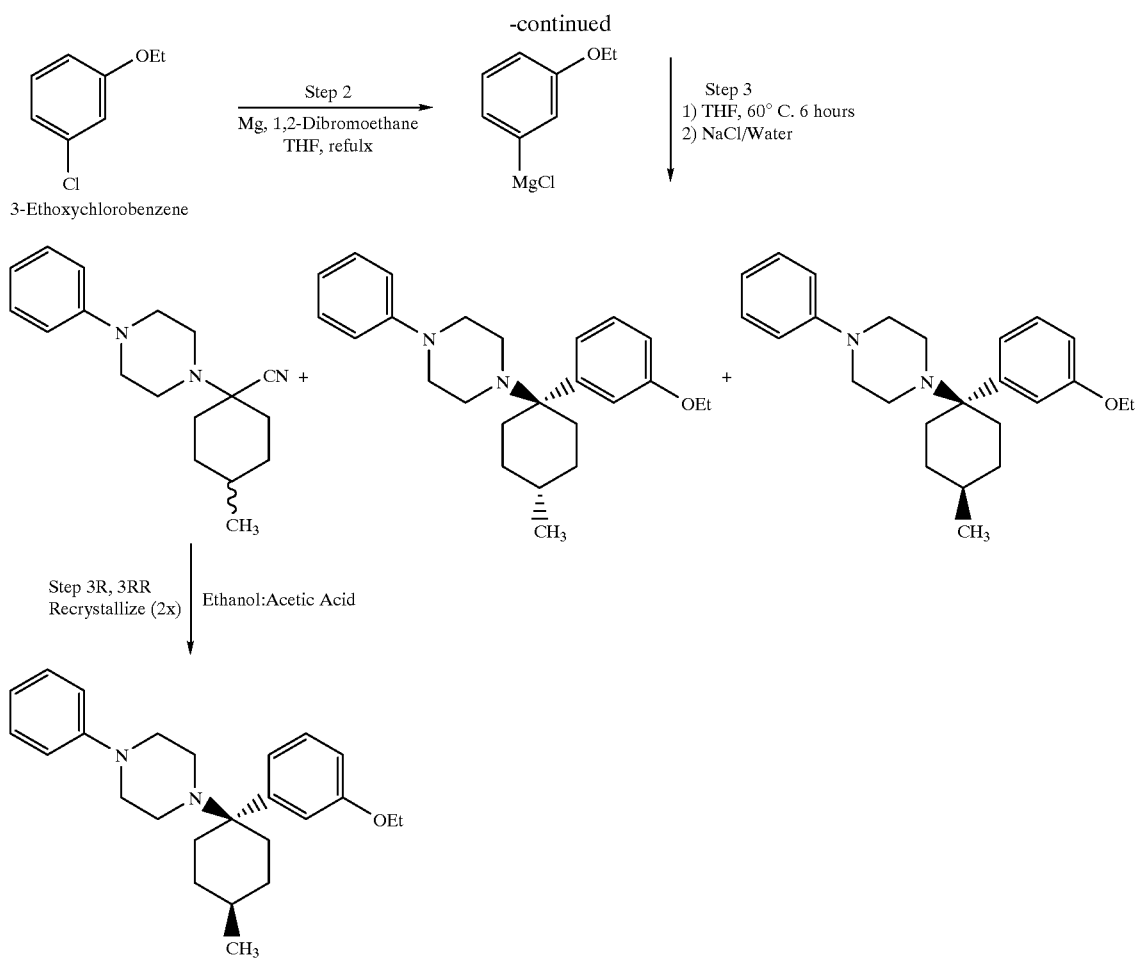

Salts of cis-1-(3-ethoxyphenyl)-1-(4-phenylpiperazin-1-yl)-4-methylcyclohexane are readily prepared by dissolving the free base in an organic solvent such as acetone or ethylacetate or a mixture of solvents. A stoichiometric amount of the counter, ion is added. Precipitation of the salt occurs quickly and the initial precipitate is then redissolved and reprecipitated.

Previously known salts of cis-1-(3-ethoxyphenyl)-1-(4-phenylpiperazin-1-yl)-4-methyl-cyclohexane have been found to be insoluble and/or of poor chemical stability. For example, the fumarate salt has low solubility (40 μg/ml) in water and low bioavailability in dogs (2%–18%). The dihydrochloride has good water solubility (1 mg/ml) and bioavailability in dogs (75%), but was found to be unstable in the solid state.

We have found that the dimesylate salt (compound I) has a solubility of 31 mg/ml, good stability and bioavailability; these superior properties make it useful for pharmaceutical applications.

Two polymorphs of the dimesylate salt have been discovered and characterized. Form A proved to be the preferred form. The use of acetone as an isolation solvent usually precipitates either form B or a mixture of forms B and A. Both forms have unique X-ray diffraction patterns and melting points. The DSC (Differential Scanning Calorimetry) of form B reveals a melt onset at 145° C. followed by a recrystallization of the melt to form A and a final melt of form A at 164.7° C. These events were confirmed using fusion microscopy. Compounds A and B have the x-ray diffraction d-spacing as shown in table 1 and 2.

TABLE 1

| Form A d-spacing of 8 largest peaks |
| --- |
| 11.01 |
| 8.735 |
| 5.941 |
| 4.869 |
| 4.667 |
| 4.272 |
| 4.116 |
| 3.614 |

TABLE 2

| Form B d-spacing of 10 largest peaks |
| --- |
| 11.38 |
| 7.957 |
| 6.913 |
| 5.650 |
| 5.466 |

TABLE 2-continued

Form B
d-spacing of
10 largest peaks 4.623
4.267
4.216
4.094
3.919

Evaluation of form A at high humidities indicated that the salt is non-hygroscopic at humidities below 90%. Chemical stability was conducted at 70° C., at ambient humidity and 40° C. in 75% RH, and in a light box under fluorescent light with no detectable degradation. Aqueous solubility of the isolated form A of the dimesylate salt is 31 mg/ml.

As the compound I is an effective neuropeptide Y1 receptor antagonist, it is of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of compound I. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders may include:

disorders or diseases pertaining to the heart, blood vessels or the renal system, such as vasospasm, heart failure, shock, cardiac hypertrophy increased blood pressure, angina, myocardial infarction, sudden cardiac death, arrhythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin. See U.S. Pat. No. 5,504,094.

The pharmaceutical utility of compound I is indicated by the following assay for human NPY1 receptor activity.

Assay for Human NPY1 Receptor Binding Activity

Membrane Preparation: Baculovirus-infected Sf9 cells expressing recombinant human NPY Y1 receptors were harvested at 42–48 hours at which time batches of 500 mL of cell suspension were pelleted by centrifugation. Each pellet was resuspended in 30 mL of lysis buffer (10 mM HEPES, 250 mM sucrose, 0.5 $\mu$g/ml leupeptin, 2 $\mu$g/ml Aprotonin, 200 $\mu$M PMSF and 2.5 mM EDTA, pH 7.4) and gently homogenized by 50 strokes using a Dounce homogenizer. The homogenate was centrifuged at 4° C. for 10 minutes at 536×g to pellet the nuclei. The supernatant was collected into a fresh tube and centrifuged twice in the same buffer at 48,000×g for 40 minutes. The final pellet was resuspended in 10 mL of PBS containing 5 mM EDTA by Dounce homogenization and stored in aliquots at –80° C.

[$^{125}$I] PYY Binding Assay: Purified membranes were washed by PBS and resuspended by gentle pipetting in binding buffer [50 mM Tris(HCl), 5 mM KCl, 120 mM NaCl, 2 mM CaCl$_2$, 1 mM MgCl$_2$, 0.1% bovine serum albumin (BSA), pH 7.4]. Membranes (5 $\mu$g) were added to siliconized (Sigmacote, Sigma) polypropylene tubes in addition to 0.050 nM [$^{125}$I] PYY(porcine) for competition analysis or 0.0100–500 nM [$^{125}$I]PYY (porcine) for saturation analysis. For evaluation of guanine nucleotide effects on receptor affinity, GTP was added at a final concentration of 100 $\mu$M. Cold displacers were added at concentrations ranging from $10^{-12}$ M to $10^{-6}$ M to yield a final volume of 0.250 mL. Nonspecific binding was determined in the presence of 1 $\mu$M NPY(human) and accounted for less than 10% of total binding. Following a 2 hour incubation at room temperature, the reaction was terminated by rapid vacuum filtration. Samples were filtered over presoaked GF/C Whatman filters (1.0% polyethylenemine for 2 hours) and rinsed 2 times with 5 mLs cold binding buffer lacking BSA. Remaining bound radioactivity was measured by gamma counting. To estimate the Bmax, Kd and Ki, the results of binding experiments were analyzed using SigmaPlot software (Jandel).

Compound I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising compound I and a pharmaceutically acceptable carrier. The pharmaceutical compositions containing compound I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

Compound I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compound I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the age, body weight, general health, sex, diet, time of administration, route of administration, and rate of excretion, drug combination and the severity of the particular disease undergoing therapy.

EXAMPLE 1

Cis-1-(3-ethoxyphenyl)-1-(4-phenylpiperazin-1-yl)-4-methyl-cyclohexane a. 1-(1-Cvano-4-methylcyclohexyl)-4-phenyl piperazine: N-Phenylpiperazine (37 ml, 40 g, 245 mmol) was suspended in 300 ml water. The pH was adjusted to between 3 and 4 using 10% HCl and 25% NaOH. 4-Methyl cyclohexanone (30 ml, 27 g, 244 mmol) was added followed by KCN (16 g, 245 mmol). The mixture was stirred 15 hours at room temperature during which time the product solidified. The product was collected by filtration, washed with water, triturated with 2-propanol, filtered, then dried in the vacuum oven overnight at 50° C. to give 58 g (84% yield) of the desired product as a roughly 2:1 mixture of diastereomers. Tlc Rf=0.25 and .3 in 9:1 Hexane:Ethyl Acetate.

b. 3-Bromo-ethoxy benzene: Sodium hydride (18.4 g 60% oil dispersion, 460 mmol) was suspended in 1000 mL DMF and cooled to 0° C. 3-Bromophenol (72 g, 419 mmol) was placed in a dropping funnel, melted with a heat gun, and added dropwise. After addition, the mixture was stirred 30 min at 0° C. Ethyl iodide (40 mL, 78 g, 503 mmol) was then added dropwise, and the mixture was stirred 12 hours allowing to warm to room temperature. The reaction was then quenched by careful addition of water (1000 ml), then extracted 4X500 ml EtOAc. The organic layers were washed 8×200 ml H$_2$O, dried over Na$_2$SO$_4$, filtered, then concentrated. The residue was distilled under house vacuum collecting the fraction boiling >120° C. to give 70 g desired product (84% yield). Density=1.47 g/ml.

c. Magnesium turnings (3.4 g, 140 mmol) were suspended in 20 ml dry THF under argon. Dibromoethane (2 ml, 7 mmol) was added to activate the magnesium. 3-Bromoethoxy benzene (20 g, 13.5 ml, 99 mmol) was added dropwise. After complete addition, the mixture was diluted with 80 ml dry THF and refluxed for two hours. The solution was cooled to room temperature and 1-(1-cyano-4-methylcyclohexyl)-4-phenyl piperazine (20 g, 70 mmol) was added as a solid all at once. The reaction was stirred at 70° C. for 12 hours, and then cooled to 0° C. and quenched by slow addition of NH$_4$Cl solution until two phases formed. The solid was filtered off and discarded, and the filtrate was concentrated. The residue was dissolved in ethanol (500 ml). Potassium hydroxide (20 g, 350 mmol) was added and the mixture was heated to 60° C. for four hours. The mixture was cooled to room temperature and concentrated. The residue was suspended in cold water and filtered. The solid was washed with cold ethanol then recrystallized from a 100:0.4 2-propanol:acetic acid to give 14.5 g pure title product m.p.=79–80° C.

EXAMPLE 2

Dimesylate salt of cis-1-(3-ethoxyphenyl)-1-(4-phenylpiperazin-1-yl)-4-methylcyclohexane A 6 g portion of the product of Example 1 was charged to 90 ml of acetone producing a clear solution. 2.3 ml (3.55 eq) of methanesulfonic acid was added. Crystallization commenced immediately. The resulting slurry was stirred under ambient conditions over night. The product was collected by filtration and dried in vacuo at 45° C. The weight yield was 7.3 g, 97.3%. This material was shown to be Form B by DSC and x-ray diffraction.

Conversion to Form A

Form B may be converted to Form A in either isopropanol or ethyl acetate under ambient conditions for 72 hours or more efficiently in the following manner. A 5 g portion of Form B was charged to 150 ml of ethyl acetate. The slurry was then heated to reflux for 15 minutes. The heat was removed and the slurry was allowed to cool to ambient over about 1 hour. The slurry was granulated under ambient conditions for 2 hours and the product collected by filtration. The weight yield was 4.41 g, 88.2%. This material was shown to be Form A by DSC and X-ray diffraction.

We claim:

1. The compound which is form B of cis-1-(3-ethoxyphenyl)-1-(4-phenylpiperazin-1-yl)-4 methylcyclohexane dimesylate.

2. The compound which is form A of cis-1-(3-ethoxyphenyl)-1-(4-phenylpiperazin-1-yl)-4 methylcyclohexane dimesylate.

3. A pharmaceutical composition comprising the compound of claim 2 and a pharmaceutically acceptable carrier.

4. A method of treating a physiological condition in a mammal characterized by the presence of an excess of neuropeptide Y which comprises administering to a mammal in need of such treatment an effective amount of the compound of claim 2.

5. A method of preparing the compound of claim 2 which comprises:

a. suspending the compound which is form B in a solvent;

b. optionally heating said suspension; and c. isolating said compound of claim 2.

6. The method of claim 6 wherein the solvent is ethyl acetate.

7. A method of claim 4 wherein said physiological condition is an eating disorder.

* * * * *